United States Patent
Rauker et al.

(10) Patent No.: US 6,689,098 B2
(45) Date of Patent: *Feb. 10, 2004

(54) OCCLUSION DEVICE

(75) Inventors: Robert M. Rauker, Maple Grove, MN (US); Peter J. Gafner, Ham Lake, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 13 days.

This patent is subject to a terminal disclaimer.

(21) Appl. No.: 10/280,189

(22) Filed: Oct. 25, 2002

(65) Prior Publication Data

US 2003/0040703 A1 Feb. 27, 2003

Related U.S. Application Data

(63) Continuation of application No. 09/512,994, filed on Feb. 24, 2000, now Pat. No. 6,475,185.

(51) Int. Cl.⁷ ............................................. A61H 29/00
(52) U.S. Cl. ..................................... 604/96.01; 604/528
(58) Field of Search .................... 128/898, 207.14; 604/506, 507, 20, 509, 96.01, 500, 508, 99.04, 915, 164.01, 164.1; 606/45, 205, 192, 194

(56) References Cited

U.S. PATENT DOCUMENTS

| | | |
|---|---|---|
| 3,044,468 A | 7/1962 | Birtwell |
| 3,087,492 A | 4/1963 | Garth |
| 3,192,949 A | 7/1965 | De See |
| 3,211,150 A | 10/1965 | Foderick |
| 3,726,282 A | 4/1973 | Patel |
| 3,799,171 A | 3/1974 | Patel |
| 3,908,267 A | 9/1975 | Loyd et al. |
| 3,982,544 A | 9/1976 | Dyck |
| 4,026,298 A | 5/1977 | Grausz |
| 4,028,037 A | 6/1977 | Dawson |
| 4,088,135 A | 5/1978 | O'Neill |
| 4,205,683 A | 6/1980 | O'Neill |
| 4,205,691 A | 6/1980 | Patel |
| 4,318,410 A | 3/1982 | Chin |
| 4,333,452 A | 6/1982 | Au |
| 4,445,892 A | 5/1984 | Hussein et al. |
| 4,506,691 A | 3/1985 | Tseo |
| 4,517,979 A | 5/1985 | Pecenka |
| 4,614,188 A | 9/1986 | Bazell et al. |
| 4,646,742 A | 3/1987 | Packard et al. |

(List continued on next page.)

FOREIGN PATENT DOCUMENTS

| | | |
|---|---|---|
| EP | 0 272 112 A2 | 6/1988 |
| EP | 0 402 467 A1 | 12/1990 |
| EP | 0 547 358 A3 | 6/1993 |
| EP | 0 547 358 A2 | 6/1993 |

(List continued on next page.)

*Primary Examiner*—Sang Y. Paik
*Assistant Examiner*—Leonid M Fastovsky
(74) *Attorney, Agent, or Firm*—Crompton, Seager & Tufte, LLC

(57) ABSTRACT

An occlusion device for occluding a body conduit including an elongate tubular shaft having an inflatable balloon disposed near the elongate shaft distal end and a proximal seal having a sufficiently small profile to allow a second catheter to pass over the distal occlusion device while the inflatable balloon remains uninflated. One occlusion device includes an elongate fluid displacement rod within the occlusion device elongate shaft, providing both a fluid pressure source and a seal. The elongate rod can be rapidly advanced and retracted, providing rapid and controlled inflation and deflation of the distal balloon. Also provided are alignment devices for aligning inflation fluid sources with occlusion device tubular proximal ends which can inject fluid through the device into the distal balloon.

13 Claims, 5 Drawing Sheets

U.S. PATENT DOCUMENTS

| | | |
|---|---|---|
| 4,696,304 A | 9/1987 | Chin |
| 4,710,168 A | 12/1987 | Schwab et al. |
| 4,723,547 A | 2/1988 | Kullas et al. |
| 4,800,109 A | 1/1989 | Washizu |
| 4,856,510 A | 8/1989 | Kowalewski |
| 4,902,095 A | 2/1990 | Baker et al. |
| 4,921,483 A | 5/1990 | Wijay et al. |
| 4,923,498 A | 5/1990 | Gregory |
| 4,968,306 A | 11/1990 | Huss et al. |
| 5,015,233 A | 5/1991 | McGough et al. |
| 5,022,422 A | 6/1991 | di Palma |
| 5,059,176 A | 10/1991 | Winters |
| 5,061,240 A | 10/1991 | Cherian |
| 5,085,636 A | 2/1992 | Burns |
| 5,120,323 A | 6/1992 | Shockey et al. |
| 5,160,321 A | 11/1992 | Sahota |
| 5,167,239 A | 12/1992 | Cohen et al. |
| 5,171,221 A | 12/1992 | Samson |
| 5,259,839 A | 11/1993 | Burns |
| 5,297,546 A * | 3/1994 | Spofford et al. ...... 128/207.014 |
| 5,304,198 A | 4/1994 | Samson |
| 5,306,246 A * | 4/1994 | Sahatjian et al. ........ 604/96.01 |
| 5,320,604 A | 6/1994 | Walker et al. |
| 5,324,255 A | 6/1994 | Passafaro et al. |
| 5,336,174 A | 8/1994 | Daoud et al. |
| 5,378,238 A | 1/1995 | Peters et al. |
| 5,423,742 A | 6/1995 | Theron |
| 5,449,343 A | 9/1995 | Samson et al. |
| 5,496,310 A * | 3/1996 | Exconde et al. ............ 606/205 |
| 5,536,252 A | 7/1996 | Imran et al. |
| 5,545,133 A | 8/1996 | Burns et al. |
| 5,695,468 A | 12/1997 | Lafontaine et al. |
| 5,709,653 A * | 1/1998 | Leone ......................... 604/20 |
| 5,718,683 A | 2/1998 | Ressemann et al. |
| 5,785,685 A | 7/1998 | Kugler et al. |
| 5,807,330 A | 9/1998 | Teitelbaum |
| 5,833,644 A | 11/1998 | Zadno-Azizi et al. |
| 5,833,650 A | 11/1998 | Imran |
| 5,925,016 A | 7/1999 | Chornenky et al. |
| 5,944,716 A * | 8/1999 | Hektner ....................... 606/45 |
| 6,027,476 A | 2/2000 | Sterman et al. |
| 6,050,972 A | 4/2000 | Zadno-Azizi et al. |
| 6,056,721 A | 5/2000 | Shulze |
| 6,090,083 A | 7/2000 | Sell et al. |
| 6,102,891 A | 8/2000 | van Erp |
| 6,176,843 B1 | 1/2001 | DiCaprio et al. |
| 6,260,552 B1 * | 7/2001 | Mortier et al. .............. 128/898 |
| 6,319,228 B1 | 11/2001 | Kastenhofer |
| 6,355,014 B1 | 3/2002 | Zadno-Azizi et al. |
| 6,475,185 B1 | 11/2002 | Rauker et al. |
| 2001/0041862 A1 | 11/2001 | Glickman |

FOREIGN PATENT DOCUMENTS

| | | |
|---|---|---|
| EP | 0 569 030 A1 | 11/1993 |
| EP | 0 710 490 A3 | 5/1996 |
| EP | 0 710 490 A2 | 5/1996 |
| EP | 0 769 307 A2 | 4/1997 |
| GB | 2 139 725 A | 11/1984 |
| GB | 2 277 875 A | 11/1994 |
| JP | 56-152655 A | 11/1981 |
| JP | 1-232927 A | 9/1989 |
| WO | WO 92/13589 A1 | 8/1992 |
| WO | WO 97/44082 A2 | 11/1997 |
| WO | WO 97/44085 A2 | 11/1997 |
| WO | WO 98/38930 A1 | 9/1998 |
| WO | WO 99/26692 A1 | 6/1999 |
| WO | WO 99/42161 A2 | 8/1999 |
| WO | WO 99/45835 A2 | 9/1999 |

* cited by examiner

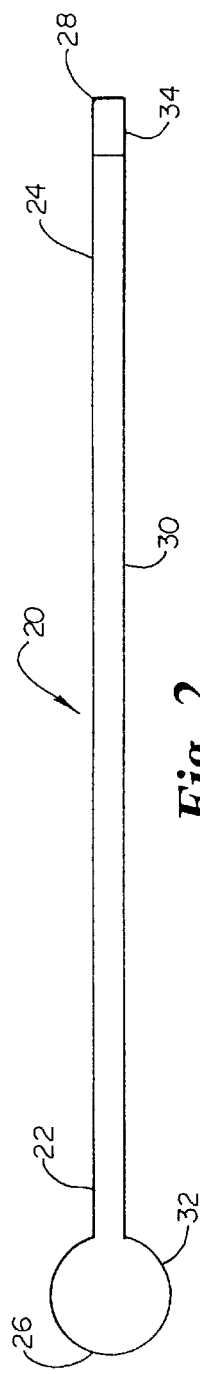
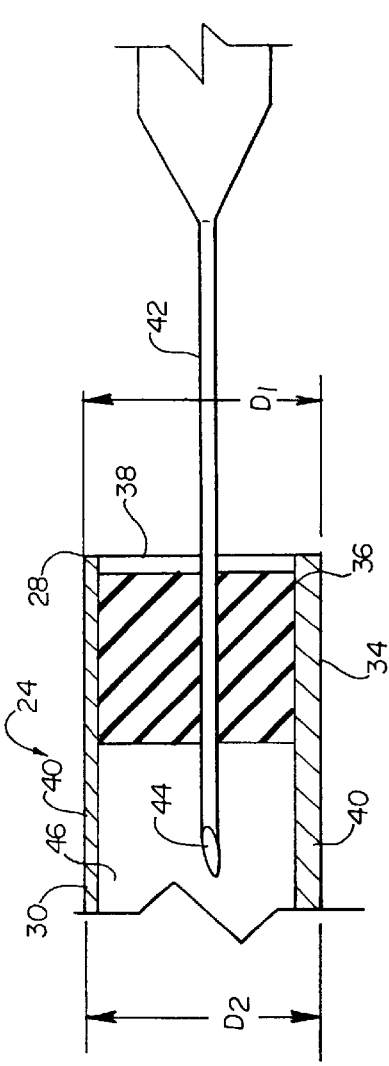
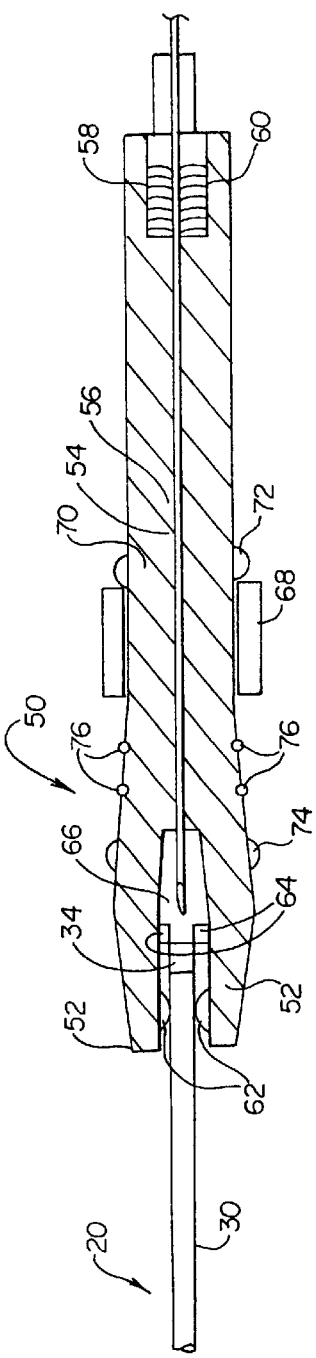
Fig. 1
Fig. 2
Fig. 3

OCCLUSION DEVICE

RELATED APPLICATIONS

This application is a continuation of 09/512,994 filed Feb. 24, 2000 now U.S. Pat. No. 6,475,185. The present application is related to U.S. application Ser. No. 08/308,025, filed Sep. 16, 1994, entitled BALLOON CATHETER WITH IMPROVED PRESSURE SOURCE, now U.S. Pat. No. 5,545,133; U.S. application Ser. No. 08/586,514, filed Jan. 16, 1996, entitled BALLOON CATHETER WITH IMPROVED PRESSURE SOURCE, now U.S. Pat. No. 5,695,468; and U.S. application Ser. No. 08/812,390, filed Mar. 5, 1997, entitled BALLOON CATHETER WITH IMPROVED PRESSURE SOURCE, now U.S. Pat. No. 5,785,685, the disclosures of which are hereby incorporated by reference.

FIELD OF THE INVENTION

The present invention is related generally to medical devices. More specifically, the present invention is directed to occlusion catheters. Catheters of the present invention incorporate devices and methods allowing a balloon or other occlusion device to be inflated or expanded and remain inflated or expanded while a second catheter is advanced over the proximal end of the occlusion catheter.

BACKGROUND OF THE INVENTION

Body vessels and conduits, for example coronary arteries, the carotid artery, and lumens of the biliary tree, are frequently treated from within using catheters having means for treating conditions or affected areas at locations within the vessels. Treatment device examples include angioplasty balloons, stents and associated stent delivery catheters, drug delivery catheters, atherectomy devices, and devices for crushing or dissolving blockages in the biliary tree. When using these and other devices, it may be desirable to position and expand an occlusion device such as an inflatable distal occlusion balloon in proximity to the device. In coronary artery applications, the occlusion device can be disposed distally and downstream of the more proximal treatment apparatus such as a rotatable atherectomy burr or an angioplasty balloon. In this application, the occlusion device is a distal occlusion device. A distal occlusion device may also be placed downstream of a stent and associated stent delivery catheter while the stent is being expanded against the vessel wall.

Distal occlusion devices can be used to prevent byproducts of treatment from leaving the treatment area. For example, small particles of plaque may be freed by an atherectomy process. Distal occlusion devices may also be used to provide a quiescent region of a body vessel where treatment can occur. In one example, a coronary artery region may be blocked off from blood flow to allow treating a stenosed region vessel wall with an agent to inhibit restenosis. In another example, a stone may be isolated between a distal and a proximal occlusion balloon, with the space being filled with a chemical to dissolve the stone. In many of these applications, the vessel region proximal of the distal occlusion device is aspirated through a catheter lumen to remove byproducts prior to deflating or removing the distal occlusion device.

An alternative application of an occlusion device is disclosed by Parodi et al. in published PCT Application WO 99/45835. The Parodi et al. disclosure is directed to an occlusion device to guard against embolization during carotid angioplasty. The occlusion device is placed within the vessel lumen proximal to the treatment site, and the device is expandable against the vascular duct to occlude the anterograde blood flow while a vacuum suction device is used to reverse blood flow distal of the occlusion device. The occlusion device includes a mouth for drainage of the retrograde blood flow containing any emboli therein. In this way, the protective device allows the temporary reversal of the flow of blood to prevent emboli from reaching the brain and allows for the drainage of emboli to the outside of the patient's body. During treatment with an angioplasty balloon distal of the occlusion device, the occlusion device in conjunction with vacuum suction and monitoring of the patient's blood flow allows controlled reversal of the blood flow.

Inflating an occlusion device is often accomplished in a manner similar to inflating an angioplasty balloon. Proximal manifolds and adapters such as Luer fittings can provide a secure channel between a pressurized fluid supply outside the body and the distal occlusion device such as a balloon. Luer fittings are often bulky and significantly larger than the tubes to which they are attached. Because it may be required to advance a second catheter over the occlusion catheter while the occlusion catheter remains in place, it is generally not possible to advance a second catheter over the occlusion catheter while the conventional fitting is attached. If the conventional fitting were removed from the occlusion device catheter shaft, the distal occlusion device shaft proximal end would require sealing to avoid loss of inflation pressure. The seal itself would have to be small enough to allow the second catheter to pass over the seal while the seal maintained the pressure within the occlusion device and balloon.

Examples of a low profile occlusion device are described by Zadno-Azizi et al. in published PCT Application No. WO 99/26692 and by Teitelbaum in U.S. Pat. No. 5,807,330. Both the Zadno-Azizi et al. and Teitelbaum devices never become completely sealed systems during operation. Both devices have proximal ports that must be opened and closed when inflating or deflating the occlusion balloon.

What would be advantageous is an occlusion catheter having a proximal end profile sufficiently small so as to allow a second catheter to be advanced over the proximal end of the occlusion balloon catheter shaft, while maintaining the occlusion balloon in an inflated state. A device allowing inflation and rapid deflation while a catheter is inserted over the distal occlusion catheter would be desirable as well. A device that does not require opening and closing a part to operate the balloon would also be desirable.

SUMMARY OF THE INVENTION

The present invention provides occlusion devices for occluding body conduits and vessels. The devices include expandable distal portions and an elongate tubular shaft. The occlusion devices allow other devices to be advanced over and retracted from the occlusion device shafts while the occlusion devices occlude the conduit or vessel. One device includes an elongate tubular shaft having an inflatable occlusion device disposed near the distal end and a lumen extending within the shaft walls. An elongate fluid displacement rod is disposed within the shaft. The fluid displacement rod is preferably at least half the length of the tubular shaft length. The tubular shaft can have a distal fluid preparation portion near the distal balloon for infusing inflation fluid into the shaft prior to use.

In use, the elongate fluid displacement rod can be advanced distally, wherein the volume of the rod within the lumen forces an equal volume of fluid into the distally disposed balloon. The fluid displacement rod can provide precise linear control of the amount of fluid forced into the balloon and a linear relationship between the linear displacement of the rod and the fluid in the balloon. The placement of the rod also provides control of pressure within the balloon. The rod can also provide for rapid inflation of the balloon and rapid deflation of the balloon. Rapid deflation can be advantageous where it is desirable for the occlusion to be ended or reduced rapidly in order to restore fluid flow. One example of this advantage may be found in rapidly deflating a distal occlusion balloon where the balloon is occluding a coronary vessel and patient condition indicates that rapid balloon deflation may be called for.

Another aspect of the invention includes alignment devices for aligning hypodermic needles for insertion into the proximal end of occlusion devices. The hypodermic needle alignment devices are particularly suitable for use with distal occlusion devices having proximally disposed sealable or self-sealing seals.

BRIEF DESCRIPTION OF THE DRAWINGS

FIG. 1 is a schematic plan view of a representative occlusion device having a proximal seal, suitable for use with one aspect of the present invention;

FIG. 2 is a longitudinal cross-sectional view of the proximal region of the occlusion device of FIG. 1, illustrating injection of inflation fluid through a self-sealing valve;

FIG. 3 is a longitudinal cross-sectional view of a jawed alignment device for aligning the needle for penetration through the device seal of FIG. 2;

DETAILED DESCRIPTION OF THE INVENTION

Figure 4:
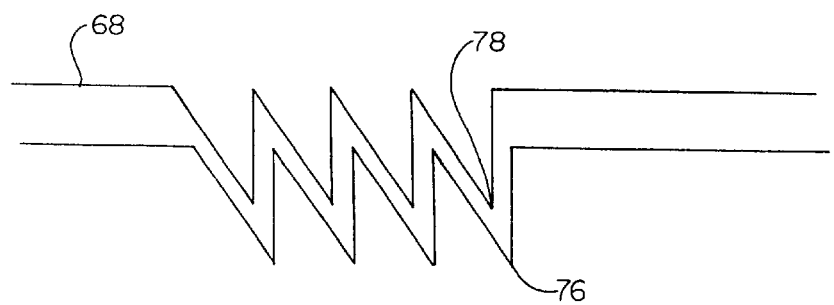
FIG. 4 is an enlarged schematic view of detents on the alignment device of FIG. 3.

FIG. 1 illustrates an occlusion device 20 having a distal region 22, a proximal region 24, a distal end 26, a proximal end 28, an elongate tubular shaft 30, a distally disposed occlusion balloon 32, and a proximally disposed seal 34. Occlusion device 20 illustrates one type of occlusion device suitable for use with a hypodermic needle alignment device, described later. Balloon 32 can be formed of a non-compliant polymeric material such as polypropylene, polyethylene and nylon or compliant polymeric materials such as polyvinyl chloride, olefin copolymers and ionomer resins, in a manner well known to those skilled in the art. The elongate tubular shaft 30 is preferably made of a material such as stainless steel hypotubing or other materials well known to those skilled in the art such as a relatively stiff polymer or a nickel titanium alloy.

FIG. 2 illustrates part of the elongate shaft proximal portion 24 of FIG. 1 in greater detail. Seal 34 can be formed of a sealable or self-sealing material such as medical grade silicone rubber or other suitable polymeric material, which is illustrated as forming a proximal plug region 36. Seal 34 can also include a proximalmost layer 38 formed of a material such as polycarbonate. Proximal seal or plug portion 36 can be formed by injecting a polymeric material between walls 40 of elongate shaft 30 to fill the lumen therein. Proximalmost film or barrier 38 can be a formed by affixing polymeric material over proximal end 28. A hypodermic needle 42 having a sharp end 44 can be inserted through seal material 36 and into a lumen 46 disposed between walls 40. In use, hypodermic needle 42 or other suitable injection device may be used to inject inflation fluid into lumen 46 to inflate balloon 32. Proximal end 38 has an outside diameter as indicated at D1. At a more distal portion within proximal region 24, elongate shaft 30 has an outside diameter D2. In one embodiment, D1 and D2 are substantially equal, elongate shaft 30 having a substantially uniform outer diameter over much of its length. In one embodiment, D1 is equal to D2. In another embodiment, D1 is only slightly larger than D2. In a preferred embodiment, D1 is not substantially larger than D2. Having the outside diameter of elongate shaft proximal end 28 substantially equal to the outside diameter of the shaft provides a small profile for advancing other devices over elongate shaft 30. In particular, in a preferred embodiment, there is no proximal seal having an outer diameter substantially larger than the outer diameter of the shaft, for example at the shaft midpoint well distal of the proximal region seal.

Having a distal occlusion device with a proximal end outside diameter approximately the same as the shaft outside diameter at its midpoint longitudinally can provide an elongate shaft which can be used for advancing a second medical device over the elongate shaft. Elongate shaft 30 can thus be used in ways similar to a guide wire. In one use, elongate shaft 30 can be used to guide a therapeutic device such as an atherectomy catheter, an angioplasty catheter, or a stent delivery catheter over the shaft. In another use, elongate shaft 30 can be used to guide a diagnostic device such as an angiography catheter over its length. "Over the wire" catheters can be guided to a target site, having shaft 30 disposed within most of their length. Single operator exchange catheters can be guided to a target site, having elongate shaft 30 disposed primarily within a distal region of the device. For such uses, it is preferred that the shaft have an outside diameter of about 0.010 inches to about 0.018 inches.

It may be possible for hypodermic needle 40 to be hand guided into proximal seal 34. Given the small dimensions of the distal occlusion device catheter shaft, however, guiding a hypodermic needle into the proximal seal can be difficult. Referring now to FIG. 3, an alignment device 50 is illustrated. Alignment device 50 can be used to guide a hypodermic needle into the proximal end of a distal occlusion device. In one embodiment, alignment device 50 includes two opposing jaws 52 disposed about elongate shaft 30. Another embodiment has three jaws, preferably spaced equidistantly about shaft 30. In other embodiments, multiple jaws, fingers, or a single cylindrical mouth may be disposed about elongate shaft 30. The alignment device illustrated includes a hypodermic needle 54 disposed within a lumen 56 extending through the central longitudinal axis of the device 50. Needle 54 has a lumen which is in fluid communication with a proximal fitting 58 which can be used for attachment to an inflation fluid source such as a syringe. In one embodiment, proximal fitting 58 includes a series of internal threads 60 for attachment of a syringe. In the distal end near the jaws, one embodiment includes a pair of alignment pads 62 for grasping shaft 30. Alignment pads 62 can be formed of elastomeric gripping material for grasping shaft 30. One embodiment also includes a pair of stops 64 for positioning the occlusion device proximal end. In the embodiment illustrated, a sharp distal end 66 of needle 56 is shown protruding toward seal 34.

In one embodiment, a clamp is included for forcing together jaws 52 about catheter shaft 30. The clamping device can be used to securely fix alignment device 50 to distal occlusion device 20 prior to inserting the needle. In one embodiment, the clamping device includes a collar or sleeve 68 disposed about alignment device 50 at a mid portion 70. Collar 68 can be disposed between a proximal stop 72 and a distal stop 74. In one embodiment, proximal stop 72 and distal stop 74 are formed as annular rings about the device. In another embodiment, discrete protruding regions or bumps form the proximal and distal stops. The alignment device can also include detents 76 securely engaging corresponding structures on the clamping collar 68. FIG. 4 illustrates in greater detail one embodiment of detents 76 and corresponding teeth 78 on the clamping collar 68. Collar 68 can also be threadably secured between stops 72 and 74. This eliminates the need for detents. As the collar is advanced across the mid portion, a wider jaw section, the jaws are forced inward to clamp on catheter shaft 30.

In use, jaws 52 can be disposed about seal 34 which is guided between alignment pads 62. With shaft 30 somewhat aligned, clamping ring 68 can be slid proximally toward jaws 52. Shaft 30 can be slid further into jaws 50 across alignment pads 62 until stops 64 is reached. In one embodiment, the distal end of needle 56 extends distally past stops 64 such that when seal 34 is finally in contact with stops 64, the distal end of needle 56 extends sufficiently far into catheter shaft 30 so as to be in fluid communication with distal occlusion device lumen 46. At this point, rings 68 can be slid distally to engage detents 76, and in some embodiments, to abut distal stops 74. With alignment device 50 securely affixed to shaft 38, fluid can be injected through needle 56, into shaft 30, into an occlusion balloon.

Figure 5:
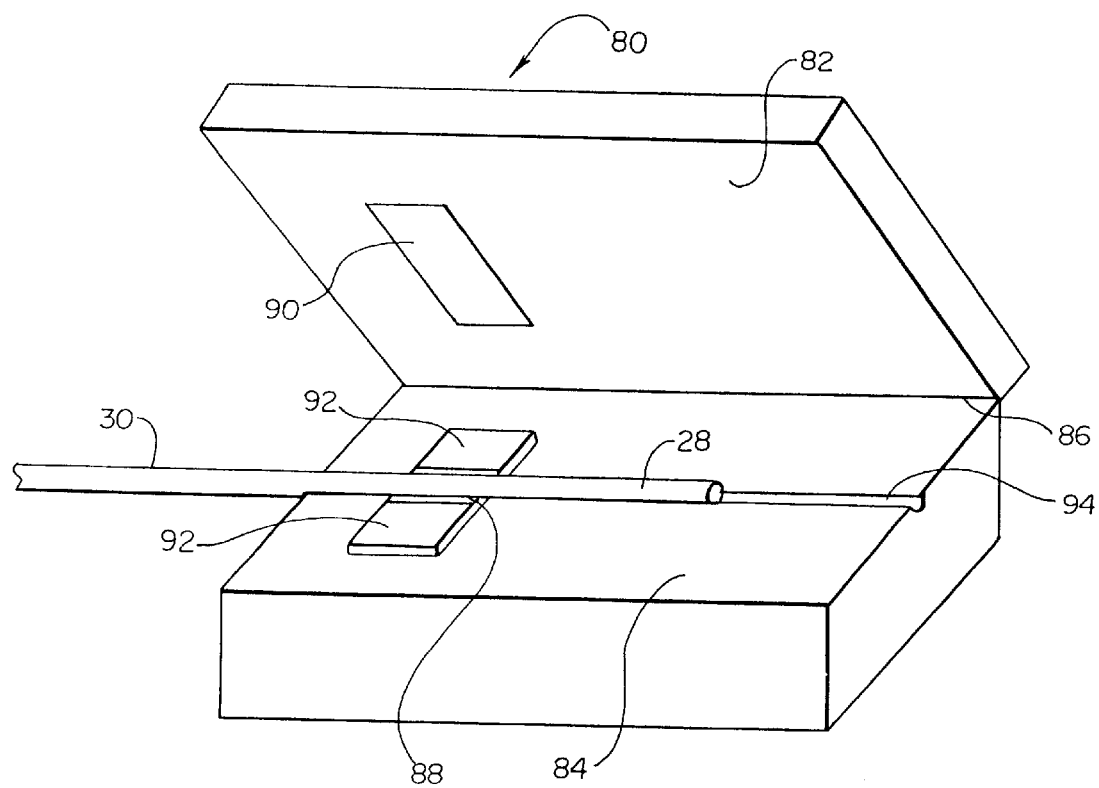
FIG. 5 is a perspective view of an alignment device for aligning a side entry hypodermic needle with the shaft of an occlusion device such as the device of FIG. 1.

Referring now to FIG. 5, another alignment device 80 is illustrated. Alignment device 80 includes a first or top surface 82 and an opposing second or bottom surface 84. Alignment device 80 includes a longitudinal channel 88 disposed on second surface 84 and a grasping pad 90 is disposed on first surface 82. Other embodiments have channels or partial channels in both the first and second surfaces and can include other means for grasping. Catheter shaft 30 is illustrated disposed longitudinally and within longitudinal channel 88. In the device illustrated, a pair of pads 92 are disposed on either side of longitudinal channel 88, with both pads 92 and 90 being formed of an elastomeric material. In one embodiment, longitudinal channel 88 allows longitudinal, but not lateral, movement of shaft 30. In another embodiment, the geometry of longitudinal channel 88 and pads 92 are such that both longitudinal and lateral movement of shaft 30 is precluded after first and second surfaces 82 and 84 are fully brought together. A second longitudinal channel 94 is illustrated, also along the longitudinal axis of shaft 30. Again, channel 94 can be formed as either a full or partial channel in both the first and second surfaces 82 and 84. In one embodiment, channel 88 and corresponding pads 92 preclude lateral and longitudinal movement of shaft 30 once enclosed, and second channel 94 allows longitudinal, but not lateral, movement of an inserted hypodermic needle.

In use, a device such as alignment device 80 can, in the open position, receive an inserted catheter shaft such as shaft 30 within longitudinal channel 80. With proximal end 28 in position, first surface 82 and second surface 84 can be closed about hinge 86, laterally and longitudinally immobilizing shaft 30. A hypodermic needle can be inserted into longitudinal channel 94, bringing the sharp tip of the hypodermic needle into shaft proximal end 28. With shaft 30 firmly held in place, inflation fluid can be injected from the hypodermic needle into shaft 30.

Figure 6:
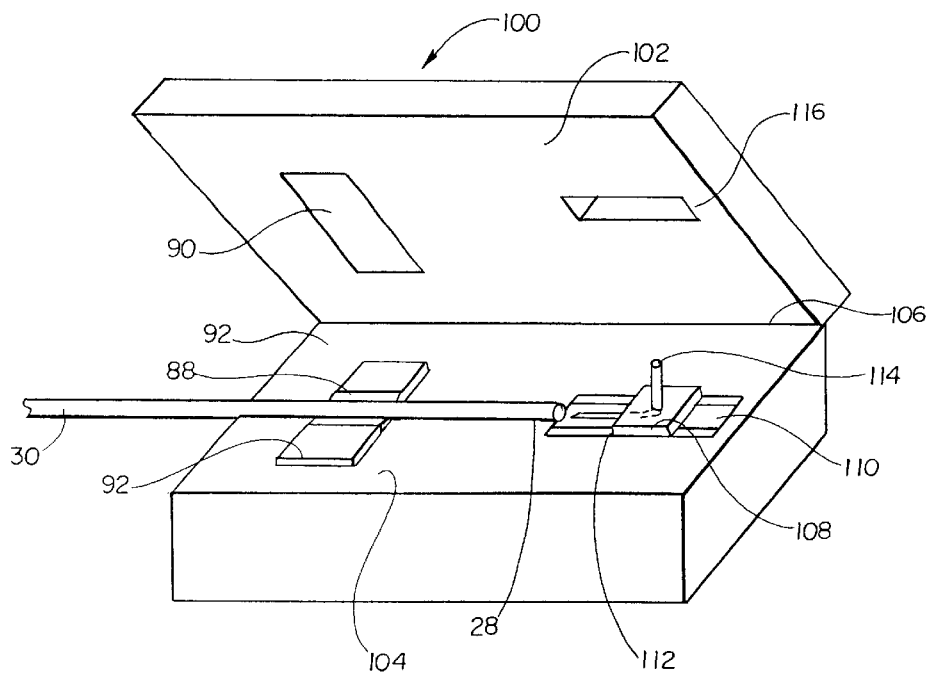
FIG. 6 is a perspective view of an alignment device for aligning a top entry, curved hypodermic needle, with the shaft of an occlusion device such as the device of FIG. 1.

Referring now to FIG. 6, another alignment device 100 is illustrated, being similar in many respects to alignment device 80 illustrated in FIG. 5. Alignment device 100 includes a first surface 102 and a second opposing surface 104, attached to each other about a hinge 106. Pads 90 and 92 can be as illustrated in FIG. 5, and as previously discussed. In the embodiment illustrated, device 100 includes longitudinal channel 88 and has a carrier 108 disposed within a second longitudinal channel 110 shown on second surface 104. Carrier 108 is preferably slidably mounted within second channel 110, providing for longitudinal movement toward and away from shaft proximal end 28. A curved or bent hypodermic needle 112 is mounted on carrier 108 and can be received within shaft proximal end 28. Hypodermic needle 112 is illustrated having a proximal port 114 which can protrude through a substantially longitudinal slot 116 in first surface 102.

In use, shaft 30 can be disposed between pads 90 and 92 within longitudinal channel 88. First surface 102 can be brought into close proximity to second surface 104, allowing hypodermic needle proximal port 114 to protrude through longitudinal slot 116. With the first and second surfaces brought together, hypodermic needle proximal port 114 can protrude through the top of device 100. A syringe or other fluid source can be attached to hypodermic needle port 114, preferably after the first and second surfaces are brought together. Before attachment of the fluid source such as a syringe, carrier 108 can be longitudinally slid toward shaft proximal end 28, causing hypodermic needle 112 to protrude sufficiently far into shaft 30. Inflation fluid can then be injected through hypodermic needle 112 and into shaft 30, inflating a distal occlusion device. Alignment device 100 has the advantage of allowing the syringe and hypodermic to be inserted into the proximal port 114 after the first and second opposing services are closed. After inflation, the fluid source can be detached from port 114, and the opposing services opened. Slidable hypodermic needle 112 can be retracted out of shaft seal region 28.

Figure 7:
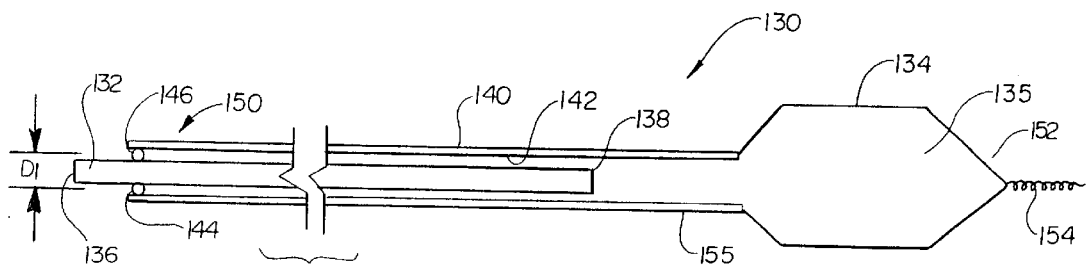
FIG. 7 is a fragmentary, longitudinal cross-sectional view of an occlusion device having a fluid displacement rod disposed within the inflation lumen.

Referring now to FIG. 7, an inflatable occlusion device 130 is illustrated, extending from a proximal region 150 to a distal region 152. Occlusion device 130 can terminate distally as illustrated, in an atraumatic tip such as a spring coil tip 154. Occlusion device 130 includes a pushable elongate rod or displacement rod 132 inserted through the device, which can be used to displace inflation fluid from the proximal portion of the shaft lumen into an occlusion balloon 134. Occlusion device 130 functions similar to the inflatable device described in U.S. Pat. No. 5,785,685 entitled BALLOON CATHETER WITH IMPROVED PRESSURE SOURCE, the disclosure of which is herein incorporated by reference in that the displacement rod movement inflates and deflates the balloon. Displacement rod 132 has an outer diameter D1 indicated near a proximal end 136 of rod 132. Rod 132 includes a distalmost end 138 illustrated as disposed distally well into device 130.

Displacement rod 132 is illustrated as directly disposed within an elongate tubular member 140 having a shaft distal region 155 proximal of balloon 134 and a lumen 142 within. Lumen 142 can serve as a means for inflating device 130, containing inflation fluid which can be displaced by rod 132 which forces fluid into distally disposed occlusion balloon 134. Inflation fluid can be retained within lumen 142 by a proximal seal 144 disposed between rod 132 and tube 140. In preferred embodiments, the displacement rod 132 is preferably pre-loaded into lumen 142 during manufacturing, with fluid filling the shaft lumen. Alternatively, the catheter could be prepped on-site. In either application, proper function of the displacement rod requires venting substantially all compressible gas from the lumen and balloon interior. One such method and device is disclosed in U.S. Pat. No. 5,785,685, wherein a one-way valve is provided to force gas from the distal portion of the catheter out the proximal end by injection of fluid through the one-way valve.

In use, occlusion device 130 can also be prepared by injecting inflation fluid into lumen 142 sufficient to largely fill the length of the lumen. After the initial filling with inflation fluid, displacement rod distal end 132 can be displaced near a proximal end 146 of outer tube 140. After device 130 is inserted well into the body, displacement rod 132 can be advanced distally, thereby forcing inflation fluid from lumen 142 into balloon 134, thereby inflating balloon 134. As can be seen in FIG. 7, displacement rod 132 provides a small proximal profile for device 130, which can allow a second catheter to be inserted over outer tube proximal end 146, thereby using outer tube 140 as a guide wire to guide a second catheter into position.

Other methods and devices can also be used to prepare the occlusion device 130 for use. Inflation fluid can be injected into tube 140 after pulling a vacuum on tube 140 and balloon 134, using methods well known to those skilled in the art. Inflation fluid can also be initially injected into outer tube 140 using features and procedures described in U.S. patent application Ser. No. 09/208,145, filed Dec. 9, 1998, entitled CATHETER WITH DISTAL MANIFOLD PREP VALVE/MANIFOLD, the disclosure of which is herein incorporated by reference. As described in the aforementioned application, inflation fluid can be injected into tube 140 through an additional valve disposed near catheter shaft distal region 144. Injecting inflation fluid from a distal location has the advantage of forcing any air proximally out of the shaft.

Distal occlusion device 130 can be both rapidly inflated and deflated, relative to a syringe inflated catheter of similar dimensions. Using a fluid displacement rod as the inflation fluid pressure source can also provide control over balloon inflation through control over linear position of the fluid displacement rod. In particular, the ability to rapidly deflate the balloon can be advantageous in coronary artery applications, where patient indications may require rapid deflation of the balloon.

Figure 8:
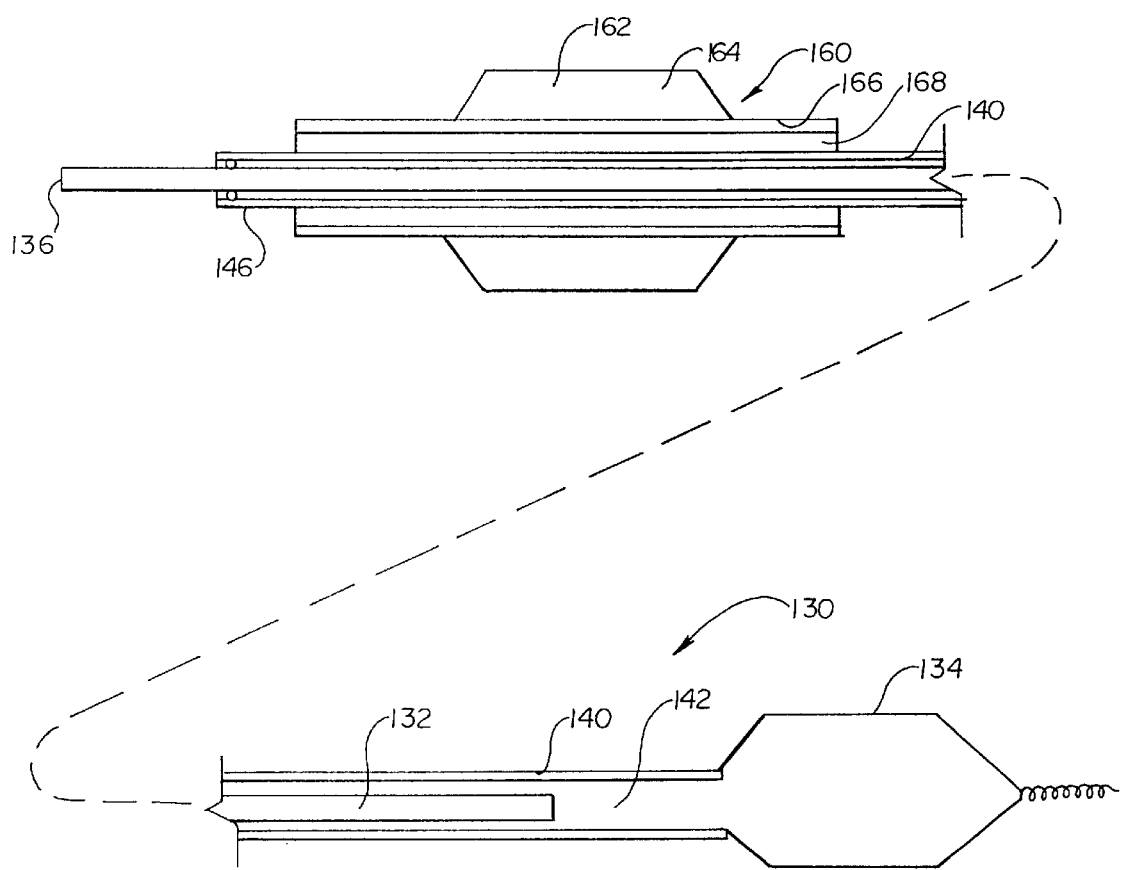
FIG. 8 is a fragmentary, longitudinal cross-sectional view of the occlusion device of FIG. 7, having a second catheter disposed over the occlusion device shaft.

Referring now to FIG. 8, distal occlusion device 130 is further illustrated having a second catheter 160 disposed over outer tube 140. Second catheter 160 can be a therapeutic or diagnostic catheter. In the example illustrated, second catheter 160 is a highly diagrammatically illustrated angioplasty balloon catheter, having only the distal region illustrated. Second catheter 160 includes a distal balloon 162 having interior 164 which is disposed about an elongate tube 166 having a lumen 168 for receiving a guide wire and/or outer tube 140 of the first or occlusion catheter 130. FIG. 8 illustrates how a second catheter can be inserted over the distal occlusion catheter where the distal occlusion catheter proximal profile is sufficiently small so as to fit within the lumen of the second catheter. In some embodiments, not requiring illustration, after displacement rod 132 is moved distally further into occlusion device lumen 142, the displacement rod proximal end can be clamped in a desired position to maintain inflation of distal occlusion balloon 134 while enclosed by outer tube 146.

Figure 9:
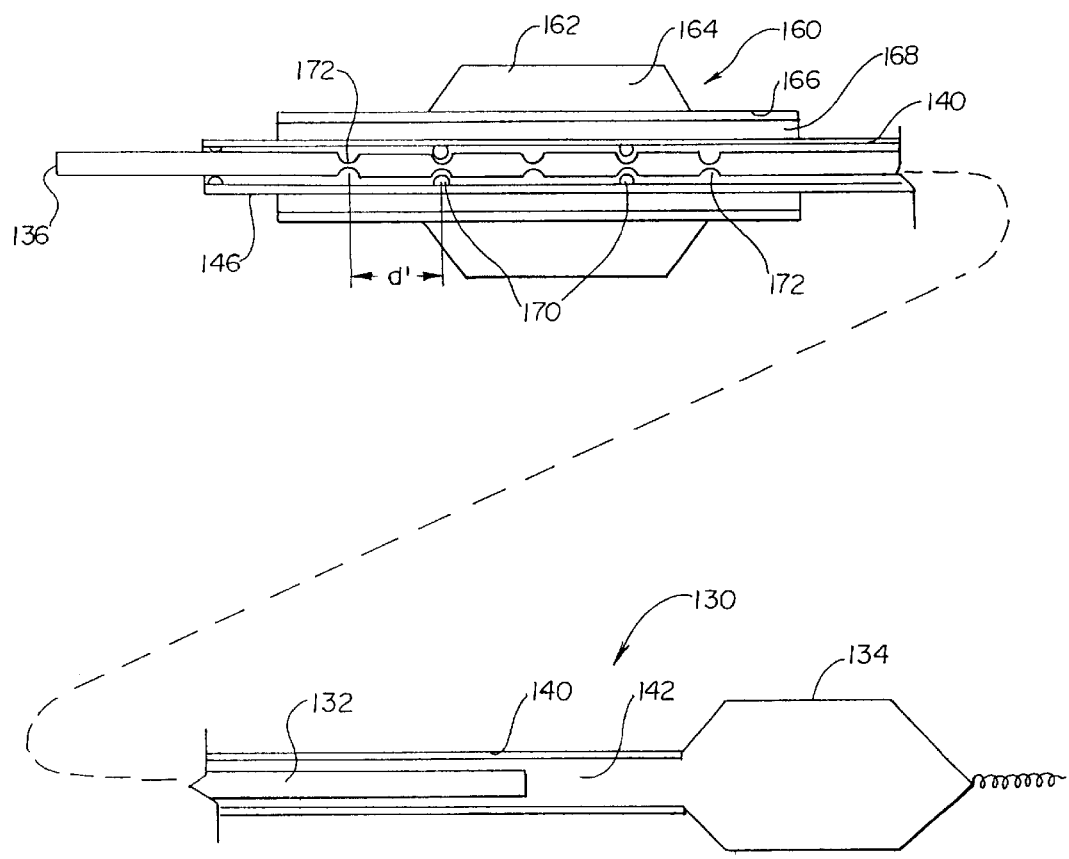
FIG. 9 is a fragmentary, longitudinal cross-sectional view of the device of FIG. 8, incorporating features to incrementally inflate the occlusion balloon.

Referring now also to FIG. 9, an alternative embodiment of the catheter of FIG. 8 is depicted. The embodiment of FIG. 9 includes the additional feature of radial expansion of balloon 134 being incrementally controlled through a ratcheting or detent mechanism 170 that interacts with corresponding indentations 172 on displacement rod 132. As shown in FIG. 9, the detents include projections extending radially inward. One or more of such detents can be incorporated in combination with one or more indentations on the displacement rod. The combination of detents and indentations can also act to enhance the desired seal 144, necessary for use. Thus, in alternative embodiments, the combination of detents and indentations could replace the seal or work in combination with the seal. The distance d' between detents 170 are preferably set to correspond to certain degrees of radial expansion of balloon 134. For example, each distance d' rod 132 is moved in a proximal to distal direction could correspond to a 0.5 mm increase in diameter of balloon 134. Correspondingly, each distance d' displacement rod 132 is moved in the distal to proximal direction would result in a 0.5 mm decrease. Other mechanisms for controlling incremental changes in radial expansion of balloon 134 include markings on the side of displacement rod 132. A threaded design is also possible.

In use, distal occlusion catheter 130 preparation can include first filling the catheter with inflation fluid while maintaining balloon 134 in an uninflated state. Fluid displacement rod 132 can be inserted into a proximal portion of outer tube 140. The distal occlusion device with rod partially inserted can be advanced past a target site in a body conduit such as a coronary artery. Second catheter 160 can be advanced over first catheter outer tube 140, receiving outer tube 140 within lumen 168. Second catheter 160 can be advanced to a treatment site, and distal occlusion device 130 can be inflated by advancing rod 132 distally within tube 140. With the vessel occluded, catheter 160 can be used to treat the target site. In some applications, for example, this may include either angioplasty or atherectomy.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A device for injecting fluid into a catheter shaft proximal port, said device having a distal end and a proximal end comprising:

at least two jaws sized for grasping said catheter shaft, said jaws disposed about a longitudinal axis;

a hypodermic needle disposed along said longitudinal axis, said hypodermic needle having a lumen therethrough, a sharp distal end, and a proximal end; and a fitting disposed near said device proximal end for coupling to a syringe, said fitting having a lumen in fluid communication with said hypodermic needle lumen.

2. The device of claim 1, wherein the jaws have a portion having a distally increasing outer extent and the device includes a slidable sleeve having an inner wall disposed proximal of the jaw increasing outer extent portion and dimensioned such that sliding the sleeve distally causes the sleeve inner wall to contact the jaw outer extent and force the jaws together about the catheter tube.

3. The device of claim 2, wherein the distally increasing outer extent comprises detents and the sleeve inner wall comprises corresponding structure, and wherein sliding the sleeve distally causes the corresponding sleeve inner wall structure to interact with the outer extent detents to force the jaws together about the catheter tube.

4. The device of claim 3, wherein the detents comprise sawtooth protrusions that extend outward from the distally increasing outer extent and the corresponding sleeve inner wall structure comprises complementary sawtooth protrusions that extend inward from the sleeve inner wall.

5. The device of claim 2, wherein the distally increasing outer extent comprises a distal stop and a proximal stop and the slidable sleeve is disposed therebetween.

6. The device of claim 2, wherein the slidable sleeve is threadedly engaged with the distally increasing outer extent.

7. A method for treating a body vessel target region comprising the steps of:
providing a first catheter including a first elongate tubular shaft having a proximal region, a distal region, and a first lumen therethrough, an inflatable balloon disposed near said first shaft distal region and having an interior in fluid communication with said first lumen, and a self-sealing seal disposed in said first catheter shaft proximal region adapted to receive a hypodermic needle and reseal after retraction of said hypodermic needle;
providing a second catheter having a second elongate tubular shaft having a distal region and a second lumen therethrough and having means for treating said vessel region disposed near said second shaft distal region;
providing an alignment device for aligning said hypodermic needle with said first catheter lumen, wherein said alignment device includes at least two jaws for grasping said catheter shaft and having said hypodermic needle disposed between said jaws;
advancing said first catheter to a position distally past said target region;
aligning said needle with said first lumen, wherein said aligning step includes grasping said catheter shaft between said jaws, and aligning said catheter with said hypodermic needle;
advancing said hypodermic needle into said first lumen using said alignment device;
inflating said first catheter balloon by inserting said hypodermic needle into said first catheter seal and providing fluid to said first catheter balloon;
retracting said hypodermic needle from said first catheter seal;
maintaining said first catheter balloon inflation by maintaining fluid pressure in said first catheter balloon;
advancing said second catheter over said first catheter shaft by inserting said first catheter shaft proximal end into said second catheter shaft lumen distal end; and
treating said vessel site with said second catheter treating means.

8. The method of claim 7, wherein said alignment device includes a clamp for forcing said jaws together about said catheter shaft, and said method further includes clamping said jaws together about said catheter shaft using said clamp.

9. A method for treating a body vessel target region comprising steps of:
providing a first catheter including a first elongate tubular shaft having a proximal region, a distal region, and a first lumen therethrough, an inflatable balloon disposed near said first shaft distal region and having an interior in fluid communication with said first lumen, and a self-sealing seal disposed in said first catheter shaft proximal region adapted to receive a hypodermic needle and reseal after retraction of said hypodermic needle;
providing a second catheter having a second elongate tubular shaft having a distal region and a second lumen therethrough and having means for treating said vessel region disposed near said second shaft distal region;
providing an alignment device for aligning said hypodermic needle with said first catheter lumen, wherein said alignment device includes a pair of opposing surfaces, at least one of said pair of surfaces having means for holding said shaft and said hypodermic needle laterally immobile and along the same longitudinal axis and means for sliding said hypodermic needle and catheter shaft together;
advancing said first catheter to a position distally past said target region;
aligning said needle with said first lumen, wherein said aligning step includes placing said catheter shaft into said alignment device, and aligning said catheter with said hypodermic needle;
advancing said hypodermic needle into said first lumen using said alignment device;
inflating said first catheter balloon by inserting said hypodermic needle into said first catheter seal and providing fluid to said first catheter balloon;
retracting said hypodermic needle from said first catheter seal; and
maintaining said first catheter balloon inflation by maintaining fluid pressure in said first catheter balloon.

10. The method of claim 9, wherein said alignment device holds said catheter shaft longitudinally immobile and allows said hypodermic needle to move longitudinally.

11. A device for treating a body vessel region while occluding a more distal body vessel region comprising:
a first catheter including a first elongate tubular shaft having a proximal region, a distal region, a proximal end, and a first lumen therethrough, an inflatable balloon disposed near said first shaft distal region and having an interior in fluid communication with said first lumen, a fluid displacement rod having a portion thereof slideably disposed in said tubular member such that said balloon may be expanded upon longitudinal actuation of said rod, and a ratcheting mechanism; and
a second catheter including a second elongate tubular shaft having a second lumen therethrough, wherein said second catheter second lumen is dimensioned to slide over said first catheter shaft while said first catheter balloon remains inflated with inflation fluid;
wherein the ratcheting mechanism permits incremental balloon expansion.

12. The device of claim 11, wherein the ratcheting mechanism comprises detents present on an interior surface of the first lumen and corresponding indents on an outer surface of the fluid displacement rod.

13. A device for treating a body vessel region while occluding a more distal body vessel region comprising:

a catheter including an elongate tubular shaft having a proximal region, a distal region, a proximal end, and a lumen therethrough;

an inflatable balloon disposed near said shaft distal region and having an interior in fluid communication with said lumen;

a fluid displacement rod having a portion thereof slideably disposed in said tubular member such that said balloon may be expanded upon longitudinal actuation of said rod; and a self-sealing seal connected to said tubular member proximal end adapted to receive a hypodermic needle and reseal after retraction of the hypodermic needle;

wherein the self-sealing seal has an external diameter that is substantially equal to an external diameter of the elongate tubular shaft.

* * * * *